United States Patent [19]

Charmot

[11] Patent Number: 5,232,782
[45] Date of Patent: Aug. 3, 1993

[54] MAGNETIZABLE "CORE-SHELL" MICROSPHERES BASED ON A CROSS-LINKED ORGANOPOLYSILOXANE AND A PROCESS FOR THEIR PREPARATION

[75] Inventor: Dominique Charmot, Paris, France

[73] Assignee: Rhone-Poulenc Chimie, Courbevoie Cedex, France

[21] Appl. No.: 634,910

[22] Filed: Dec. 27, 1990

[30] Foreign Application Priority Data

Dec. 27, 1989 [FR] France .................. 89 17232

[51] Int. Cl.$^5$ ............................... B32B 25/20
[52] U.S. Cl. ................... 428/405; 428/407; 427/213.34; 252/62.54
[58] Field of Search ............ 427/213.34; 428/405, 428/407; 252/62.54

[56] References Cited

U.S. PATENT DOCUMENTS

| | | | |
|---|---|---|---|
| 3,159,601 | 12/1964 | Ashby | 260/46.5 |
| 3,159,662 | 12/1964 | Ashby | 260/448.2 |
| 3,220,972 | 11/1965 | Lamoreaux | 260/46.5 |
| 3,296,291 | 1/1967 | Chalk et al. | 260/448.2 |
| 3,344,111 | 9/1967 | Chalk | 260/46.5 |
| 3,436,366 | 4/1969 | Modic | 260/37 |
| 3,480,555 | 11/1969 | Jackson et al. | 252/62.56 |
| 3,715,334 | 2/1973 | Karstedt | 260/46.5 UA |
| 3,775,452 | 11/1973 | Karstedt | 260/429 R |
| 3,814,730 | 6/1974 | Karstedt | 260/46.5 UA |
| 3,928,629 | 12/1975 | Chandra et al. | 427/387 |
| 4,094,804 | 6/1978 | Shimoiizaka | 252/62.52 |
| 4,177,317 | 12/1979 | Schoenafinger et al. | 428/405 |
| 4,272,601 | 6/1981 | Tokura et al. | 428/407 |
| 4,654,267 | 3/1987 | Ugelstad et al. | 428/407 |
| 4,677,003 | 6/1984 | Redlich et al. | 428/407 |
| 4,695,392 | 9/1987 | Whitehead et al. | 428/405 |
| 4,985,166 | 1/1991 | Leising et al. | 428/405 |
| 5,034,145 | 7/1991 | Leising et al. | 428/405 |

FOREIGN PATENT DOCUMENTS

| | | |
|---|---|---|
| 0125995A3 | 11/1984 | European Pat. Off. . |
| 0319828A2 | 6/1989 | European Pat. Off. . |
| 3002477A1 | 8/1980 | Fed. Rep. of Germany . |
| 1313846 | 11/1962 | France . |
| 88676 | 1/1967 | France . |
| 1480409 | 4/1967 | France . |
| 2618084 | 1/1989 | France . |
| 2624873 | 6/1989 | France . |

OTHER PUBLICATIONS

PCT Application No. PCT/US86/02093 entitled "Magnetic-Polymer Particles."

Primary Examiner—John C. Bleutge
Assistant Examiner—Karen A. Dean
Attorney, Agent, or Firm—Finnegan, Henderson, Farabow, Garrett & Dunner

[57] ABSTRACT

Magnetizable "core-shell" microspheres comprising a core of a magnetizable filler and a shell of crosslinked organopolysiloxane obtained by dispersing an aqueous suspension of a magnetizable filler, not coated with a dispersing agent, in an organic solvent, dissolving an organopolysiloxane and an organohydrogenpolysiloxane in the organic phase, crosslinking, removing water, separating and, if appropriate, redispersing the magnetizable microspheres in water.

27 Claims, No Drawings

MAGNETIZABLE "CORE-SHELL" MICROSPHERES BASED ON A CROSS-LINKED ORGANOPOLYSILOXANE AND A PROCESS FOR THEIR PREPARATION

BACKGROUND OF THE INVENTION

The present invention relates to magnetizable "core-shell" particles based on crosslinked organopolysiloxane, useful alone or in an aqueous dispersion. The present invention also relates to a process for the preparation of magnetizable "core-shell" particles and their application to biology.

In French Patent Application No. 2,624,873, the assignee of the present invention described magnetizable composite particles based on crosslinked organopolysiloxane, said particles consisting of a matrix originating from the hydrosilylation of an organopolysiloxane and an organohydrogenpolysiloxane and, encapsulated in said matrix, magnetizable fillers coated with a dispersing agent insoluble in water. The presence of this dispersing agent can be a drawback for use in biology because the agent can migrate towards the surface of the particles and give rise to side reactions.

The Applicant has now found composite microspheres of which the core comprises a magnetizable filler not coated with a hydrophobic surfactant.

SUMMARY OF THE INVENTION

According to the invention, the microspheres concerned are magnetizable microspheres based on crosslinked organopolysiloxane, either alone or in aqueous dispersion, each microsphere comprising:

(1) a core comprising a magnetizable filler having a size preferably smaller than $300 \times 10^{-4}$ μm, more preferably about $50 \times 10^{-4}$ to $120 \times 10^{-4}$ μm, and (2) a shell based on a crosslinked organopolysiloxane derived from hydrosilylation of at least one organopolysiloxane SiVi of the following formula I:

$$R'R_2 Si\ O(Si\ R\ R''\ O)_n (Si\ R'\ R''\ O)_m Si\ R_2\ R' \qquad (I)$$

in which formula:

the R radicals are identical or different and are selected from a $C_1$-$C_4$ alkyl radical, specifically a 3,3,3-trifluoropropyl radical, and a phenyl radical;

the R, radicals may be identical or different and are selected from a $C_1$-$C_4$ alkyl radical, specifically a 3,3,3-trifluoropropyl radical, a phenyl radical, and a vinyl radical, wherein the number of vinyl radicals is at least 2 per macromolecule;

with at least 60% of the radicals R and R' being methyl radicals;

the R'' radicals may be identical or different and are selected from a $C_1$-$C_4$ alkyl radical specifically a 3,3,3-trifluoropropyl radical, a phenyl radical, and an -r-X unit, wherein r is a divalent organic radical and X is selected from a non-vinyl and non-polycondensable ionic and/or a reactive group;

n and m can independently be zero, R' being a vinyl radical if m is zero, and n and m having a value sufficient to provide a polymer having a viscosity of 20 mPas to 30,000,000 mPas at 25° C., and, wherein the total number of -r-X units contributed by the organopolysiloxane SiVi and the organohydrogenpolysiloxane SiH ranges from 1:1 to 1000:1 per molecule, preferably 5 to 500 per molecule, obtained from the hydrosilylation of organopolysiloxane SiVi with organohydrogenpolysiloxane SiH; said organopolysiloxane SiVi containing SiVi groups comprising a vinyl group bonded to a silicon atom;

with at least one organohydrogenpolysiloxane SiH containing, per molecule, at least three SiH groups with each group comprising a hydrogen atom linked to a silicon atom, said organohydrogenpolysiloxane SiH having a viscosity ranging from 5 to 1,500 mPas at 25° C., preferably between 20 and 150 mPas at 25° C., and optionally carrying non-vinyl ionic and/or reactive units linked to a silicon atom or to a carbon atom of a hydrocarbon group joined to the organohydrogenpolysiloxane chain by a Si-C bond.

DESCRIPTION OF THE PREFERRED EMBODIMENTS

The following may be mentioned by way of example of organopolysiloxane SiVi:
- the polymers of formula II

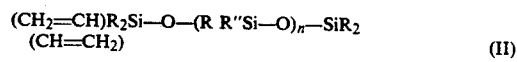

$$(CH_2=CH)R_2Si-O-(R\ R''Si-O)_n-SiR_2 \atop (CH=CH_2) \qquad (II)$$

wherein R and R'' have the definition given above, n having a value sufficient to provide a polymer viscosity of 20 mPas to 30,000,000 mPas at 25° C.,
- and the polymers of formula III

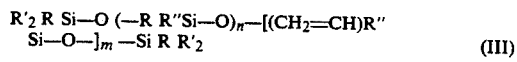

$$R'_2\ R\ Si-O\ (-R\ R''Si-O)_n-[(CH_2=CH)R'' \atop Si-O-]_m-Si\ R\ R'_2 \qquad (III)$$

wherein R, R' and R'' have the meaning given above, n and m have a value sufficient to provide a polymer viscosity of 20 mPas to 30,000,000 mPas at 25° C.

The organohydrogenopolysiloxane SiH can be a straight-chain, branched, or cyclic polymer.

Among the preferential organohydrogenopolysiloxanes SiH, those of formula IV may be mentioned by way of example:

$$Y\ R_2\ Si\ O\ (R\ R''\ SiO)_p\ (YR\ SiO)_q\ SiR_2\ Y \qquad (IV)$$

wherein:

the R radicals may be identical or different and are selected from a $C_1$-$C_4$ alkyl radical specifically a 3,3,3-trifluoropropyl radical, and a phenyl radical, with at least 80% of the R radicals being methyl radicals;

the Y radicals may be identical or different and are selected from a $C_1$-$C_4$ alkyl radical specifically a 3,3,3-trifluoropropyl radical, a phenyl radical, and a hydrogen atom, the number of hydrogen atoms being at least 3 per molecule of polymer;

and the radical R'' is selected from a $C_1$-$C_4$ alkyl radical specifically a 3,3,3-trifluoropropyl radical, a phenyl radical, and an -r-X unit, wherein r is a divalent organic radical and X is selected from a non-vinyl and non-polycondensable ionic group and/or a reactive group;

p and q having values sufficient to provide a polymer SiH having a viscosity ranging from 5 to 1,500 mPas at 25° C., preferably on the order of 20 to 150 mPas at 25° C., and, wherein the total number of -r-X units contributed by the organopolysiloxane SiVi and the organohydrogenpolysiloxane SiH ranges from 1:1 to 1000:1 per molecule, preferably on the order of 5 to 500 per molecule, obtained from the hydrosilylation of organopolysiloxane SiVi with organohydrogenophysiloxane SiH.

Divalent organic radicals represented by r within the scope of the invention include, but are not limited to, the following: straight-chain or branched $C_1$-$C_{18}$ alkylene radicals, optionally extended by 1 to 5 divalent ethylene amine groups, by 1 to 50 $C_1$-$C_3$ alkylene oxide groups or by a group

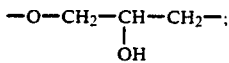

and polyoxyalkyleneradicals containing from 1 to 50 $C_1$-$C_3$ oxyalkylene units.

The following may be mentioned by way of example of divalent radicals:

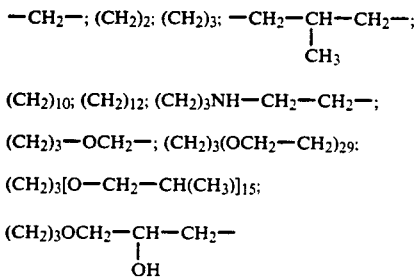

Reactive or ionic groups X within the scope of the invention include, but are not limited to, the following: epoxy, hydroxyl, carboxyl, aldehyde, ester, acetoester, mercapto, mercaptoester, amino, alkylamino, dialkylamino, trialkylamino, quaternary ammonium, aminoalcohol, amido, hydrazide, hydrazino, $C_1$-$C_3$ haloalkyl, halobenzyl, cyano,

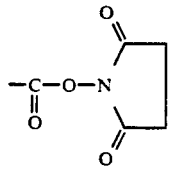

cyanato, sulphate and sulphonyl.

Polymers SiVi and SiH not bearing non-vinyl ionic and/or reactive units are well known. They are described, for example, in the U.S. Pat. Nos. 3,220,972, 3,344,111 and 3,436,366, the disclosures of which are specifically incorporated by reference herein.

Polymers SiVi and SiH bearing non-vinyl ionic and/or reactive groups can be prepared by well-known methods.

The polymers bearing non-vinyl ionic and/or reactive groups can be obtained for example by:
- equilibration of a cyclotetrasiloxane and a vinylcyclotetrasiloxane in the presence of a disiloxane containing functional groups;
- equilibration of a cyclotetrasiloxane containing functional groups in the presence of a divinyldisiloxane; or
- equilibration of a polysiloxane oil containing functional groups in the presence of a divinylsiloxane and/or a cyclotetrasiloxane.

The polymers SiH carrying non-vinyl ionic and/or reactive groups can be obtained, for example, by:
- equilibration of a cyclotetrasiloxane and a polysiloxane oil containing internal SiH functions in the presence of a disiloxane which contains functional groups and is not reactive towards SiH groups,
- equilibration of a cyclotetrasiloxane containing functional groups, not reactive towards SiH groups in the presence of a dihydrogenodisiloxane,
- equilibration of a polysiloxane oil containing functional groups, not reactive towards SiH groups, in the presence of a dihydrogenodisiloxane or of a polysiloxane containing internal SiH functions.

In one preferred embodiment of the invention, the shell based on crosslinked polyorganosiloxane is derived from the hydrosilylation of at least one organopolysiloxane SiVi and at least one organohydrogenopolysiloxane SiH, wherein the ratio of SiH groups (a hydrogen atom bonded to a silicon atom) to the SiVi groups (a vinyl group bonded to a silicon atom) preferably ranges from 0.75:1 to 4:1, more preferably from 0.75:1 to 1.5:1.

Among the materials which can make up the magnetizable filler forming the core of the particles of the invention, the following may be mentioned by way of example: magnetite, hematite, chromium dioxide, ferrites such as the manganese, nickel, manganese-zinc ferrites, alloys of cobalt, nickel, gadolinium, and samarium-cobalt. The preferred materials are magnetite and hematite. The magnetizable filler can be a mixture of fillers.

A filler having a fluorescence spectrum such as yttrium oxide or oxysulphide activated with europium, gadolinium-cerium-terbium borate, cerium-terbium aluminate, magnesium-barium aluminate doped with divalent europium, may be present along with the magnetizable filler.

The amount of magnetizable filler forming the core corresponds to about 0.5 to 98% (of which 0.01% to 0.5% is made up of optional fluorescent fillers) by weight of the filler relative to the weight of the microspheres, and preferably from 5 to 80% by weight.

The magnetizable microspheres which are the subject of Applicant's invention are substantially spherical; the microsphere can be of uniform size or have a particle size variation; the diameter can be on the order of 0.05 to 3 microns and preferably on the order of 0.2 to 2 microns.

The microspheres are useful alone or in dispersion in water; the amount of magnetizable microspheres in the dispersed state in water can correspond to about 10 to 70% by weight, relative to the total weight of dispersion, and preferably about 15 to 50% by weight.

The magnetizable "core-shell" microspheres which are the subject of Applicant's invention can be prepared by a process comprising:
dispersing an aqueous suspension of a magnetizable filler, not coated with dispersing agent, and a hydrosilylation catalyst, in a water-immiscible organic solvent, said filler having a size smaller than $300 \times 10^{-4}$ μm, preferably on the order of $50 \times 10^{-4}$ to $120 \times 10^{-4}$ μm,
dissolving a mixture of:
at least one organopolysiloxane of formula I; and at least one organohydrogenpolysiloxane SiH containing, per molecule, at least three hydrogen atoms each linked to a silicon atom, said organohydrogenpolysiloxane having a viscosity ranging from 5 to 1,500 mPas at 25° C., preferably between 10 and 150 mPas at 25° C., and optionally carrying a nonvinyl ionic and/or reactive unit bonded to a silicon atom or to a carbon atom of a hydrocarbon group linked to the organohydrogenpolysiloxane by a Si-C bond, in the organic phase of the dispersion obtained;

crosslinking the mixture of the organohydrogenpolysiloxane and organopolysiloxane polymers;

removing the water;

separating off the magnetizable microspheres; and if appropriate, redispersing said microspheres in water.

The organic solvent used in the dispersion step is a solvent for the organopolysiloxane polymers and organohydrogenopolysiloxane. The following solvents may be mentioned by way of example: cyclohexane, methylene chloride, benzene, hexane, octane, toluene, carbon tetrachloride and the esters of fatty diacids.

The dispersion step is carried out in one or more steps at a temperature ranging from about 20° to 60° C., with the aid of a vigorous agitation system such as a colloid mill, high-pressure pumps, vibratory stirrer, ultrasonic equipment.

The aqueous suspension of a magnetizable filler can be obtained by suspending a filler which has been ground up; however, a preferential form of suspension is an aqueous sol of a magnetizable filler obtained by any known process, such as, for example, that described in U.S. Pat. No. 3,480,555.

Other fillers may be present along with the magnetizable filler, such as fluorescent fillers.

The concentration of magnetizable filler in the aqueous suspension can range from about of 0.5 to 50% by weight, preferably about 5 to 20% by weight. The amount of filler used is such that the ratio by weight of the magnetizable filler to the mixture of organopolysiloxane SiVi and organohydrogenpolysiloxane SiH polymers ranges from about 0.005:1 to 50:1.

The amount of organic solvent used is such that the ratio by weight of the aqueous phase to the organic phase ranges from about 0.005:1 to 2:1.

A surfactant is used to carry out the dispersion step. The surfactant is preferably chosen from those enabling the attainment of a water-in-oil emulsion (having an HLB generally lower than 10, preferably lower than 5). Such surfactants may be nonionic agents such as fatty acid esters of sorbitol, sorbitan mono- and trioleates, ethylene oxide/propylene oxide block copolymers, ethoxylated alkylphenols containing less than 10 ethoxy units, polycondensation products of fatty acids, and the organosiloxaneethylene oxide-propylene oxide block copolymers; anionic agents, such as the dialkyl sulphosuccinates; and cationic agents such as cetylammonium bromide and polyethyleneimine-polyester copolycondensation products.

Compounds which may be used as silylation catalysts include compounds of a metal of the platinum group, preferably their salts and complexes, especially chloroplatinic acid and the platinumolefin complexes as described in the U.S. Pat. Nos. 3,159,601 and 3,159,662, the products of the reaction of derivatives of platinum with alcohols, aldehydes and ethers described in U.S. Pat. No. 3,220,972, the platinum-vinylsiloxane catalysts described in French Patent No. 1,313,846 and its addition 88,676 and French Patent No. 1,480,409 and also the complexes described in U.S. Pat. Nos. 3,715,334, 3,775,452 and 3,814,730 and a rhodium catalyst as described in U.S. Pat. Nos. 3,296,291 and 3,928,629.

The preferred metals of the platinum group are platinum and rhodium. Ruthenium, which is less active and less expensive than platinum or rhodium, can also be used.

The amount of catalyst used is preferably on the order of 5 to 100 ppm, more preferably 10 to 60 ppm, calculated as weight of metal relative to the total weight of the polymers SiVi and SiH.

In a preferred embodiment of the invention, the relative amounts of the SiVi and SiH polymers are such that the number-ratio of SiH groups (hydrogen atom bonded to a silicon atom) to the SiVi groups (vinyl group bonded to a silicon atom) is between 0.75:1 and 4:1, preferably between 0.75:1 and 1.5:1.

The crosslinking step can be carried out at a temperature ranging from 20° to 90° C., preferably 50° to 70° C. This step generally takes about 2 to 24 hours.

The water is then removed, for example, by distillation.

After cooling, the magnetizable microspheres can be separated from the organic medium by any known means, preferably by magnetization.

If desired, the magnetizable microspheres can be redispersed in deionized water until a proportion of solids of about 10 to 70% by weight, preferably about 15 to 50% by weight, is obtained. This operation is carried out in the presence of at least one surfactant, such as an alkylsulphate or an alkylsulphonate, which enables the attainment of an oil-in-water emulsion having an HLB generally higher than 10, preferably higher than 15.

The magnetizable microspheres which are the subject of Applicant's invention are of particular value in biology.

The magnetizable microspheres of the invention can be used, for example, as active supports:

. for antibodies or antigens for diagnostics tests, the separations of biological compounds by affinity; the fixation of biological molecules can, if necessary, be carried out by well-known coupling methods involving coupling agents (glutaraldehyde, water-soluble carbodiimide), or by activating any groups in the poly-organosiloxane (for example by diazotization, by the action of cyanogen bromide or hydrazine) and for reacting the molecule to be fixed.

. for enzymatic systems for biological reactions,

. for fixation of cell cultures,

. to guide medicaments or indicator substances either in vitro or in vivo towards the chosen point of treatment, . for chemical molecules enabling growth of these molecules by rapid sequences of individual reactions such as peptide synthesis, . for reaction catalysts, . for separation or the extraction of metals or optical isomers.

The microspheres of the invention can also be used as a reinforcing filler for elastomers or for the preparation of organic dispersions used in the hydraulic circuits of brakes and shock absorbers.

When the microspheres contain a luminescent filler, said microspheres can be used as a cell marker or as a contrast agent in medical imagery.

The following examples are given by way of illustration and may not be regarded as limiting the field and the spirit of the invention.

The aqueous suspension of magnetic iron oxide not treated with a surfactant, used in the examples below, was prepared in the following way:

175 g of Fe(NO$_3$)$_3$.9H$_2$O and 75 g of Fe(SO$_4$).7H$_2$O were dissolved in 250 g of ion-exchanged water and 55 g of concentrated nitric acid;

250 g of a 20% aqueous solution of ammonia were added while stirring vigorously. After settling and removing the supernatant solution, the precipitate was washed once with water. The mixture was then adjusted to pH 0.5 by means of 35 g of perchloric acid, and the precipitate was filtered off; this operation was repeated 3 times, after which the oxide was re-suspended in water and subjected to ultrafiltration by means of ion-exchanged water. The suspension thus obtained had a solids content of 26.5% at a pH of 1.2. The yield expressed as Fe$_3$O$_4$ was 57%. Examination by sizes of between $50 \times 10^{-4}$ and $200 \times 10^{-4}$ microns.

EXAMPLE 1

Preparation of "core-shell" magnetizable microspheres having a shell of crosslinked polymethylsiloxane 2 g of the iron oxide suspension prepared above mixed with 0.4 g of a 0.25% by weight aqueous solution of chloroplatinic acid was dispersed in a mixture comprising 50 g of Solvesso 200 (polyaromatic petroleum cut supplied by Esso (France)) and 0.1 g of SPAN 80 (sorbitan monooleate marketed by ICI (UK)) with the aid of an ultrasonic homogenizer. This inverse emulsion was put into a thermo-controlled 50 ml glass reactor fitted with a mechanical stirrer and a condenser. The temperature was brought to 50° C. and 5.62 g of a mixture comprising:

4.07 g of a divinyl-organosilicon oil (termed oil Si-vinyl A) of formula I:

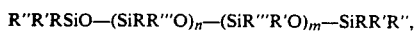

where R=R'=R'''=CH$_3$ and R''=CH:CH$_2$, with n+m=142, and 0.55 g of a divinyl-organosilicon oil (termed oil Si-vinyl B) of formula I:

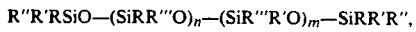

where R=R'=R'''=—CH$_3$, R''=—CH:CH$_2$, with n+m=24, and 1 g of a hydrosilylated organosilicon oil (termed oil Si-H C) of formula IV:

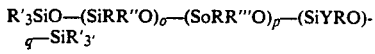

where R=R'=R''=R'''=—CH$_3$ and Y=H, with o+p=16 and q=42,
were introduced over the course of 1 hour.

The mixture was stirred for 15 h and the water present in the emulsion was then removed by azeotropic distillation. The microspheres were recovered by magnetization and were washed with acetone and redispersed in water in the presence of Cemulsol NP 30 (ethoxylated nonylphenol containing 30 molecules of ethylene oxide, marketed by SFOS (France)) in a concentration of 1 g/l to form a magnetic latex having a solids content of 10%. The hydrosilylation yield was close to 100%, expressed as weight of crosslinked poly-dimethylsiloxane at the surface of the particles.

The iron oxide content in the particles was 8% by weight, estimated by determination of iron by atomic absorption. The sizes of the particles were between 0.1 micron and 0.5 micron, measured by transmission electron microscopy.

EXAMPLE 2

Example 1 was repeated except that SPAN 80 was replaced by Hypermer LP8 (a dispersing agent marketed by ICI (UK)). The mixture of oil Si-vinyl and oil Si-H comprised 4.07 g of oil Si-vinyl A and 1 g of oil Si-H C.

The hydrosilylation yield was close to 100%, expressed as weight of crosslinked polymethylsiloxane at the surface of the particles. The iron oxide content of the particles was 9%.

EXAMPLE 3

Example 1 was repeated except that Solvesso 200 was replaced by octane. The mixture of oil Si-vinyl and oil Si-H comprised 4.54 g of oil Si-vinyl A and 0.5 g of oil Si-H C. The hydrosilylation yield was 28%, expressed as weight of crosslinked poly-dimethylsiloxane at the surface of the particles. The iron oxide content of the particles was 27%.

EXAMPLE 4

Preparation of "core-shell" magnetizable microspheres having a shell of crosslinked polydimethylsiloxane containing epoxy functional groups Example 1 was repeated except that the mixture of oil Sivinyl and oil Si-H comprised 2 g of oil Si-vinyl A, and 0.5 g of hydrosilylated and epoxidized organosilicon oil of formula

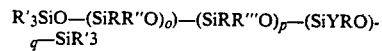

where R=R'=R''=—CH$_3$, Y=H and R'''=glycidyl ether, with o=6, p=6 and q=6.

The hydrosilylation yield was 31%, expressed as weight of crosslinked epoxidized polydimethylsiloxane at the surface of the particles. The iron oxide content in the particles was 36%.

EXAMPLE 5

Preparation of "core-shell" magnetizable microspheres having a shell of crosslinked polydimethylsiloxane containing amine functional groups 2 g of microspheres prepared in Example 4 were taken and redispersed in 50 g of toluene. The dispersion was then put into the reactor described in Example 1. The temperature was brought to 100° C.; 1.1 g of an alkoxy-diamine of formula:

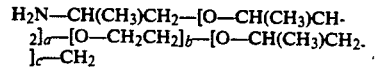

(Jeffamine marketed by Texaco (USA)) was then introduced dropwise. The reaction mixture was left at this temperature for 15 hours. After cooling, the excess amine was removed by magnetic settling. The aminated microspheres were then redispersed in water to obtain a magnetizable latex.

COMPARATIVE EXAMPLE 1

In this example the aqueous suspension of iron oxide, not treated with a surfactant, was replaced by a suspension of iron oxide treated with a surfactant and prepared in accordance with the process claimed in U.S. Pat. No. 4,094,804; it was iron oxide precipitated in the presence of oleic acid, which was repeptized in an aqueous medium by adding anionic emulsifier (dioctyl sulphosuccinate, Aerosol OT marketed by American Cyanamid). The synthesis was continued as indicated in Example 1: in this case no magnetizable microspheres were obtained; in fact, the iron oxide had diffused progressively from the aqueous phase towards the organic phase.

I claim:

1. Magnetizable microspheres comprising:
   (1) a core comprising a magnetizable filler not coated with either a hydrophobic surfactant or a dispersing agent having a size smaller than about $300 \times 10^{-4}$ μm; and
   (2) shell based on a crosslinked organopolysiloxane derived from hydrosilylation of:
      a) at least one organopolysiloxane SiVi of the following formula I:

$$R'R_2 Si O (Si R R'' O)_m Si R_2 R' \qquad (I)$$

in which formula
      the R radicals are identical or different and are selected from the group consisting of a $C_1$-$C_4$ alkyl radical and a phenyl radical;
      the R' radicals may be identical or different and are selected from the group consisting of a $C_1$-$C_4$ alkyl radical, a phenyl radical, and a vinyl radical, wherein the number of vinyl radicals is at least 2 per macromolecule;
      with at least 60% of the R and R' radicals being methyl radicals;
      the R'' radicals may be identical or different and are selected from the group consisting of a $C_1$-$C_4$ alkyl radical, a phenyl radical, and an -r-X unit, wherein r is a divalent organic radical and X is selected from the group consisting of epoxy, hydroxyl, carboxyl, aldehyde, ester, acetoester, mercapto, mercaptoester, amino, alkylamino, dialkylamino, trialkylamino, quaternary ammonium, aminoalcohol, amido, hydrazide, hydrazino, $C_1$-$C_3$ haloalkyl, halobenzyl, cyano,

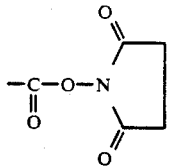

cyanato, sulphate and sulphonyl;
      n and m can independently be zero, R' being a vinyl radical if m is zero, and n and m having values sufficient to provide a polymer having a viscosity of 20 mPas to 30,000,000 mPas at 25° C.; and wherein the total number of -r-X units contributed by the organopolysiloxane SiVi and the organohydrogenpolysiloxane SiH, defined below, ranges from 1:1 to 1,000:1 per molecule obtained from the hydrosilylation of organopolysiloxane SiVi with organohydrogenpolysiloxane SiH;
      said organopolysiloxane SiVi containing SiVi groups comprising a vinyl group bonded to a silicon atom;
      b) with at least one organohydrogenpolysiloxane SiH containing, per molecule, at least three SiH groups with each group comprising a hydrogen atom linked to a silicon atom, said organohydrogenpolysiloxane having a viscosity ranging from 5 to 1,500 mPas at 25° C.

2. The microspheres according to claim 1, wherein said at least one organohydrogenpolysiloxane SiH contains a unit selected from the group consisting of epoxy, hydroxyl, carboxyl, aldehyde, ester, acetoester, mercapto, mercaptoester, amino, alkylamino, dialkylamino, trialkylamino, quaternary ammonium, aminoalcohol, amido, hydrazide, hydrazino, $C_1$-$C_3$ haloalkyl, halobenzyl, cyano,

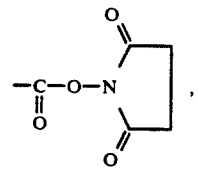

cyanato, sulphate and sulphonyl linked to a silicon atom or to a carbon atom of a hydrocarbon group joined to the organohydrogenpolysiloxane via a Si-C bond.

3. The microspheres according to claim 1, wherein the magnetizable filler has a size ranging from $50 \times 10^{-4}$ to $120 \times 10^{-4}$ microns.

4. The microspheres according to claim 1, wherein the amount of magnetizable filler making up the core is about 5 to 98% by weight of the microspheres.

5. A microsphere according to claim 1, wherein the organohydrogenpolysiloxane SiH has the formula:

$$Y R_2 Si O (R R'' SiO)_p (YR SiO)_q SiR_2 Y \qquad (IV)$$

wherein:
   the R radicals may be identical or different and are selected from the group consisting of a $C_1$-$C_4$ alkyl radical and a phenyl radical, with at least 80% of the R radicals being methyl radicals;
   the Y radicals may be identical or different and are selected from the group consisting of a $C_1$-$C_4$ alkyl radical, a phenyl radical, and a hydrogen atom, the number of hydrogen atoms being at least 3 per molecule of polymer;
   and the radical R'' is selected from the group consisting of a $C_1$-$C_4$ alkyl radical, a phenyl radical, and an -r-X unit wherein r is a divalent organic radial and X is selected from the group consisting of epoxy, hydroxyl, carboxyl, aldehyde, ester, acetoester, mercapto, mercaptoester, amino, alkylamino, dialkylamino, trialkylamino, quaternary ammonium, aminoalcohol, amido, hydrazide, hydrazino, $C_1$-$C_3$ haloalkyl, halobenzyl, cyano,

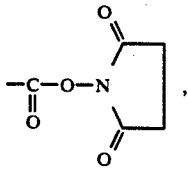

cyanato, sulphate and sulphonyl;
   p and q having values sufficient to provide a polymer SiH having a viscosity ranging from 5 to 1,500 mPas at 25° C. and, wherein the total number of -r-X units contributed by the organopolysiloxane SiVi and the organohydrogenpolysiloxane SiH ranges from 1:1 to 1000:1 per molecule obtained from the hydrosilylation of organopolysiloxane SiVi with organohydrogenpolysiloxane SiH.

6. The microspheres according to claim 1, wherein the ratio of SiH groups of the organohydrogenpolysiloxane to SiVi groups of the organopolysiloxane ranges between 0.75:1 and 4:1.

7. The process for the preparation of magnetizable microspheres comprising:

dispersing an aqueous suspension of a magnetizable filler, not coated with dispersing agent, and a hydrosilylation catalyst, in a water-immiscible organic solvent, said filler having a size smaller than $300 \times 10^{-4}$ μm to form a dispersion dissolving in said dispersion a mixture of: at least one organopolysiloxane of formula I of claim 1 and at least one organohydrogenpolysiloxane SiH, said organohydrogenpolysiloxane containing, per molecule, at least three hydrogen atoms each linked to a silicon atom, and having a viscosity ranging from 5 to 1,500 mPas at 25° C.;

crosslinking the mixture of the organohydrogenpolysiloxane and organopolysiloxane polymers, thereby forming said magnetizable microspheres;

removing the water from said aqueous suspension; and separating off the magnetizable microspheres.

8. The process according to claim 7, wherein, in dissolving the mixture, said organohydrogenpolysiloxane SiH contain units selected from the group consisting of epoxy, hydroxyl, carboxyl, aldehyde, ester, acetoester, mercapto, mercaptoester, amino, alkylamino, dialkylamino, trialkylamino, quaternary ammonium, aminoalcohol, amido, hydrazide, hydrazino, $C_1$–$C_3$ haloalkyl, halobenzyl, cyano,

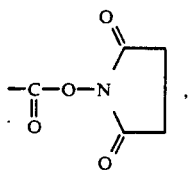

cyanato, sulphate and sulphonyl linked to a silicon atom or to a carbon atom of a hydrocarbon group jointed to the organohydrogenpolysiloxane by a Si-C bond.

9. The process according to claim 7, further comprising redispersing the separated magnetizable microspheres in water.

10. The process according to claim 7, wherein the magnetizable filler has a size ranging from $50 \times 10^{-4}$ to $120 \times 10^{-4}$ microns.

11. The process according to claim 7, wherein the concentration of magnetizable filler in the aqueous suspension is about 0.5 to 50% by weight and the amount of filler used is such that the ratio by weight of magnetizable filler to the mixture of organohydrogenpolysiloxane and organopolysiloxane polymers is about 0.005:1 to 50:1.

12. The process according to claim 7, wherein the amount of organic solvent used is such that the ratio by weight of the aqueous phase to the organic phase is about 0.005:1 to 2:1.

13. The process according to claim 7, wherein the organohydrogenpolysiloxane SiH has the formula IV:

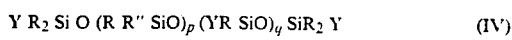

wherein:

the R radicals may be identical or different and are selected from the group consisting of a $C_1$–$C_4$ alkyl radical and a phenyl radical, with at least 80% of the R radicals being methyl radicals;

the Y radicals may be identical or different and are selected from the group consisting of a $C_1$–$C_4$ alkyl radical, a phenyl radical, and a hydrogen atom, the number of hydrogen atoms being at least 3 per molecule of polymer;

and the radical R″ is selected from the group consisting of a $C_1$–$C_4$ alkyl radical, a phenyl radical, and an -r-X unit wherein r is a divalent organic radial and X is selected from the group consisting of epoxy, hydroxyl, carboxyl, aldehyde, ester, acetoester, mercapto, mercaptoester, amino, alkylamino, dialkylamino, trialkylamino, quaternary ammonium, aminoalcohol, amido, hydrazide, hydrazino, $C_1$–$C_3$ haloalkyl, halobenzyl, cyano,

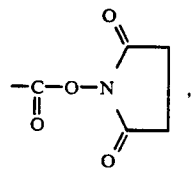

cyanato, sulphate and sulphonyl;

p and q having values sufficient to provide a polymer SiH having a viscosity ranging from 5 to 1,500 mPas at 25° C. and, wherein the total number of -r-X units contributed by the organopolysiloxane SiVi and the organohydrogenpolysiloxane SiH ranges from 1:1 to 1000:1 per molecule obtained from the hydrosilylation of organopolysiloxane SiVi with organohydrogenpolysiloxane SiH.

14. The process according to claim 7, wherein the ratio of SiH groups to SiVi groups ranges between 0.75:1 and 4:1.

15. A support for a biological or chemical substance comprising microspheres according to claim 1.

16. The microspheres of claim 1, wherein said $C_1$–$C_4$ alkyl radical R is a 3,3,3-trifluoropropyl radical.

17. The microspheres of claim 1, wherein said $C_1$–$C_4$ alkyl radical R′ is a 3,3,3-trifluoropropyl radical.

18. The microspheres of claim 1, wherein said $C_1$–$C_4$ alkyl radical R″ is a 3,3,3-trifluoropropyl radical.

19. The microspheres of claim 5, wherein said $C_1$–$C_4$ alkyl radical R is a 3,3,3-trifluoropropyl radical.

20. The microspheres of claim 5, wherein said $C_1$–$C_4$ alkyl radical Y is a 3,3,3-trifluoropropyl radical.

21. The microspheres of claim 5, wherein said $C_1$–$C_4$ alkyl radical R″ is a 3,3,3-trifluoropropyl radical.

22. The process according to claim 7, wherein in said organopolysiloxane SiVi of formula I said $C_1$–$C_4$ alkyl radical R is a 3,3,3-trifluoropropyl radical.

23. The process according to claim 7 wherein in said organpolysiloxane SiVi of formula I said $C_1$–$C_4$ alkyl radical R′ is a 3,3,3-trifluoropropyl radical.

24. The process according to claim 7, wherein in said organpolysiloxane SiVi of formula I said $C_1$–$C_4$ alkyl radical R″ is a 3,3,3-trifluoropropyl radical.

25. The process according to claim 13, wherein in said organohydrogenpolysiloxane SiH of formula IV said $C_1$–$C_4$ alkyl radical R is a 3,3,3-trifluoropropyl radical.

26. The process according to claim 13, wherein in said organohydrogenpolysiloxane SiH of formula IV said $C_1$–$C_4$ alkyl radical Y is a 3,3,3-trifluoropropyl radical; and 27. The process according to claim 13, wherein in said organohydrogenpolysiloxane SiH of formula IV said $C_1$–$C_4$ alkyl radical R″ is a 3,3,3-trifluoropropyl radical.

* * * * *

UNITED STATES PATENT AND TRADEMARK OFFICE
CERTIFICATE OF CORRECTION

PATENT NO. : 5,232,782
DATED : Aug. 3, 1993
INVENTOR(S) : Dominique Charmot

It is certified that error appears in the above-indentified patent and that said Letters Patent is hereby corrected as shown below:

Claim 7, column 11, line 15, after "organopolysiloxane" insert --SiVi--.

Claim 8, column 11, line 29, change "contain" to --contains--.

Claim 8, column 11, line 45, change "jointed" to --joined--.

Claim 26, column 13, line 4, change "radical; and" to --radical--.

Signed and Sealed this

Nineteenth Day of July, 1994

Attest:

BRUCE LEHMAN

*Attesting Officer*    Commissioner of Patents and Trademarks